United States Patent [19]

Shimada et al.

[11] Patent Number: 5,630,969

[45] Date of Patent: May 20, 1997

[54] CERAMIC HEATER PRODUCING METHOD

[75] Inventors: Takeo Shimada; Masatoshi Yanase, both of Atsugi, Japan

[73] Assignee: Unisia Jecs Corporation, Atsugi, Japan

[21] Appl. No.: 434,415

[22] Filed: May 3, 1995

Related U.S. Application Data

[62] Division of Ser. No. 189,606, Feb. 1, 1994, abandoned.

[30] Foreign Application Priority Data

Feb. 4, 1993 [JP] Japan ........................ 5-40573

[51] Int. Cl.$^6$ .................................................. C04B 41/81
[52] U.S. Cl. ........................ 264/642; 264/663; 264/676
[58] Field of Search ........................................ 264/61, 62

[56] References Cited

U.S. PATENT DOCUMENTS

| | | | |
|---|---|---|---|
| 4,507,191 | 3/1985 | Ebizawa et al. | 204/427 |
| 4,540,479 | 9/1985 | Sakurai et al. | 219/543 |
| 4,578,174 | 3/1986 | Kato et al. | 204/429 |
| 4,644,141 | 2/1987 | Hagen et al. | 219/543 |
| 4,834,863 | 5/1989 | Yamada et al. | 204/429 |
| 4,900,412 | 2/1990 | Ker et al. | 204/427 |
| 4,914,274 | 4/1990 | Hatanaka et al. | 219/270 |
| 5,027,425 | 6/1991 | Slomka | 392/480 |

FOREIGN PATENT DOCUMENTS

| | | |
|---|---|---|
| 34 37 397 | 4/1986 | Germany . |
| 38 10 736 | 10/1989 | Germany . |
| 38 43 863 | 6/1990 | Germany . |
| 39 32 880 | 4/1991 | Germany . |
| 63-146381 | 6/1988 | Japan . |

*Primary Examiner*—Donald E. Czaja
*Assistant Examiner*—Sean Vincent
*Attorney, Agent, or Firm*—Foley & Lardner

[57] ABSTRACT

A ceramic heater and a method for producing the ceramic heater. The ceramic heater includes a ceramic heater core formed in a rod shape having a bore extending axially through the heater core. The heater core has a pair of flattened portion near the rear end of the heater core. A conductive heater pattern is formed on the outer peripheral surface of the heater core. The heater pattern includes end portions formed on the respective flattened portions. The ceramic heater also includes a protective layer formed to cover the heater pattern except for the end portions, and flattened conductive terminals formed on the respective end patterns.

12 Claims, 4 Drawing Sheets

CERAMIC HEATER PRODUCING METHOD

This application is a division of application Ser. No. 08/189,606, filed Feb. 1, 1994, now abandoned.

BACKGROUND OF THE INVENTION

This invention relates to a ceramic heater suitable for use with an oxygen sensor adapted to sense the oxygen concentration of exhaust gases discharged from an internal combustion engine and a method of producing such a ceramic heater.

Normally, an oxygen sensor is located to monitor the oxygen content of the exhaust from an engine for air/fuel ratio feedback control. It is preferable to start an engine equipped with a turbo charger at an enriched air/fuel ratio. In this case, the temperature of the engine exhaust is about 280° C. and is not enough for the oxygen sensor to operate in order. It is the current practice to heat the oxygen sensor to its activation temperature (about 350° C.) with the use of a ceramic heater.

For example, Japanese Patent Kokai No. 63-146381 discloses a conventional oxygen sensor provided with a ceramic heater. The ceramic heater includes a ceramic heater core formed in a rod shape through an injection molding process. A heater pattern is printed on the outer peripheral surface of the heater core. The heater core is dipped along with the heater pattern in a ceramic slip and burnt to form a protective layer on the heater pattern. A conductive material is plated on the heater core outer peripheral surface not covered by the protective layer to form terminals for connection to a power source.

One of the difficulties encountered with such a conventional ceramic heater is the tendency toward defective contact since the terminals have curved surfaces. In addition, such a conventional ceramic heater has a great thermal capacity which requires a long time for the heater pattern to heat the oxygen sensor to its activation temperature. Furthermore, it is very difficult to uniform the thickness of the protective layer formed on the heater core on which the heater pattern has been printed without severe temperature and humidity control for the ceramic slip.

SUMMARY OF THE INVENTION

It is a main object of the invention to provide an improved ceramic heater which is free from defective contact problems, can achieve an activation temperature in a shorter time, and can be produced with higher efficiency.

Another object of the invention is to provide a method of producing such an improved ceramic heater.

There is provided, in accordance with the invention, a ceramic heater comprising a ceramic heater core formed in a rod shape having first and second cavities elongated axially thereof. The first cavity opens at the rear end of the heater core, and the second cavity opens at the front end thereof. The heater core has a pair of flattened portion near the rear end of the heater core. A conductive heater pattern is formed on the outer peripheral surface of the heater core. The heater pattern includes end portions formed on the respective flattened portions. The ceramic heater also includes a protective layer formed to cover the heater pattern except for the end portions, and flattened conductive terminals formed on the respective end patterns.

In another aspect of the invention, the ceramic heater comprises a ceramic heater core formed in a rod shape having a bore extending axially through the heater core. The heater core has a pair of flattened portion near the rear end of the heater core. A conductive heater pattern is formed on the outer peripheral surface of the heater core. The heater pattern includes end portions formed on the respective flattened portions. The ceramic heater also includes a protective layer formed to cover the heater pattern except for the end portions, and flattened conductive terminals formed on the respective end patterns.

In another aspect of the invention, there is provided a method of producing a ceramic heater. The method comprises the steps of molding a ceramic heater core in a rod shape having first and second cavities elongated axially thereof, the first cavity opening at the rear end of the heater core, the second cavity opening at the front end thereof, the heater core having a pair of flattened portion near the rear end of the heater core; printing a heater pattern made of a conductive material on the outer peripheral surface of the heater core while rotating the heater core about the first and second cavities, the heater pattern including end portions formed on the respective flattened portions; printing a protective layer to cover the heater pattern except for the end portions; and burning the heater core along with the printed protective layer.

In still another aspect of the invention, the ceramic heater producing method comprises the steps of molding a ceramic heater core in a rod shape having a bore extending axially through the heater core, the heater core having a pair of flattened portion near the rear end of the heater core; printing a heater pattern made of a conductive material on the outer peripheral surface of the heater core while rotating the heater core about the axial bore, the heater pattern including end portions formed on the respective flattened portions; printing a protective layer to cover the heater pattern except for the end portions; and burning the heater core along with the printed protective layer.

BRIEF DESCRIPTION OF THE DRAWINGS

This invention will be described in greater detail by reference to the following description taken in connection with the accompanying drawings, in which.

DETAILED DESCRIPTION OF THE INVENTION

Figure 1:
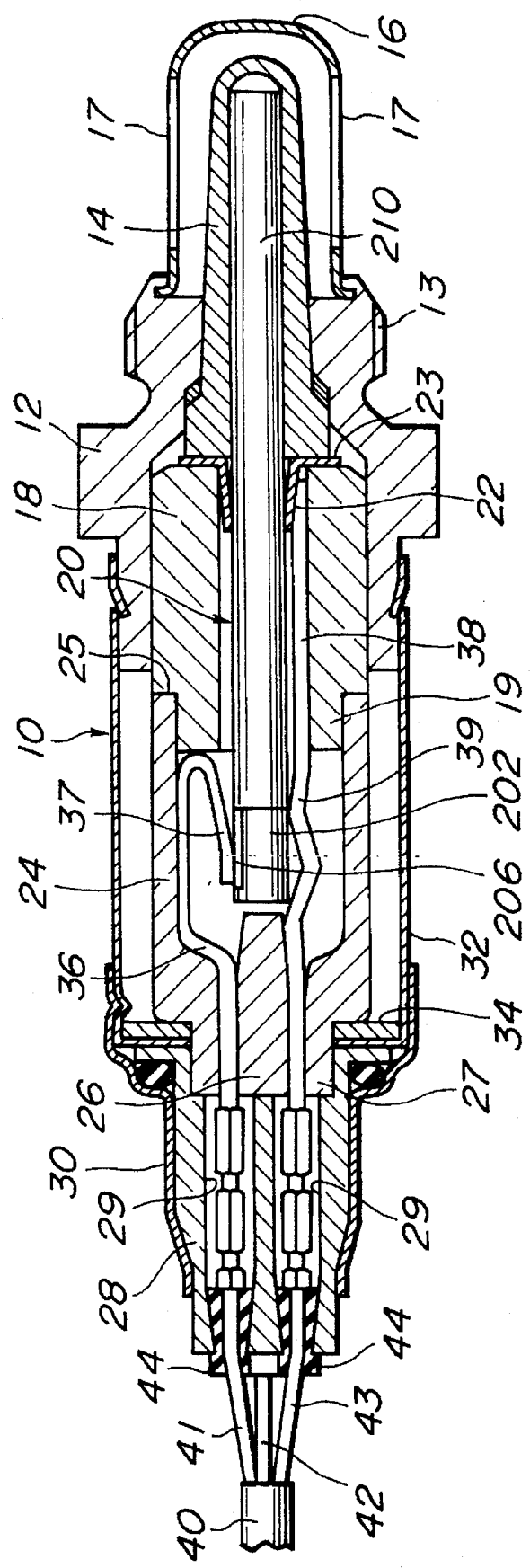
FIG. 1 is a longitudinal sectional view showing an oxygen sensor employing one embodiment of a ceramic heater made in accordance with the invention.

With reference to the drawings, and in particular to FIG. 1, there is shown an oxygen sensor employing one embodiment of a ceramic heater made in accordance with the invention. The oxygen sensor, generally designated by the numeral 10, includes a cylindrical holder 12 provided near its front end with an externally threaded portion 13 for attachment to the exhaust passage (not shown) of an internal combustion engine. A sensor probe 14 is fitted through a washer in the cylindrical holder 12 and it extends from the cylindrical holder 12. The sensor probe 14, which may be made of a ceramic material such as zirconium oxide or the like, has inner and outer electrodes (not shown) formed respectively on the inner and outer surfaces thereof. The inner electrode is connected to a conductive sleeve 22 to be described later, whereas the outer electrode is grounded through the cylindrical holder 12. The sensor probe 14 is covered with a protection cover 16 mounted on the front surface of the cylindrical holder 12. The protection cover 16, which may be made of a metal material such as stainless steel or the like, is formed in its peripheral surface with elongated windows 17 for exposure of the sensor probe 14 to the exhaust gases discharged through the exhaust passage from the engine to the atmosphere. In the presence of an oxygen concentration difference between the exhaust gases and the atmosphere, the sensor probe 14 produces a corresponding electromotive force between its inner and outer electrodes.

The cylindrical holder 12 also has an insulating cylinder 18 fitted therein. The insulating cylinder 18 may be made of a ceramic material such as alumina or the like. A ceramic heater 20 extends through the insulating cylinder 18 into the sensor probe 14 for heating the sensor probe 14 at a desired temperature. The ceramic heater 20 is positioned in place by a tapered conductive sleeve 22 formed at its front end with an annular flange 23 fixed between the rear end of the sensor prove 14 and the front end of the insulating cylinder 18. The ceramic heater 20 includes a heater core 202, terminals 206, a heater pattern 208 and a protective layer 210 to be described later in greater detail. The insulating cylinder 18 is formed at its rear end with a small-diameter portion 19 on which an insulating cylindrical cover 24 is fitted. The insulating cylindrical cover 24 may be made of a ceramic material such as alumina or the like. The insulating cylindrical cover 24 is open at its front end 25 fitted on the insulating cylinder 18 and formed at its rear end 26 with a small-diameter portion 27 fitted in a cylindrical end seal 28 covered with an outer cap 30. A cylindrical cap 32 is fixed at its front end on the peripheral surface of the rear portion of the cylindrical holder 12 and at its rear end on the peripheral surface of the small-diameter portion 27 of the insulating cylindrical cover 24. A disc spring 34 is placed on the small-diameter portion 27 of the insulating cylindrical cover 24 between the cylindrical cap 32 and the insulating cylindrical cover 24 to urge the insulating cylinder 18 through the insulating cover 24 axially in the forward direction so as to hold the insulating cylinder 18, the insulating cylindrical cover 24 and the sensor probe 14 in position. The cylindrical end seal 28 is made of a fluororesin such as polytetra fluoroethylene. The cylindrical end seal 28 has three through-holes 29 equally spaced at 120 degrees.

A pair of contact springs, one of which is shown at 36, have turned portions 37 placed in the insulating cover 24. The turned portion 37 has a wide area held in contact with the terminal 206 of the heater core 202. The contact springs 36 extends into the corresponding through-holes 29 through the rear end 26 of the insulating cover 24 and they are connected to a source of power through lead wires 41 and 42. A contact plate 38 extends through the insulating cylinder 18 in to contact with the conductive sleeve 22 and extends through the rear end 26 of the insulating cover 24 into the corresponding through-hole 29. The contact plate 38 has a curved portion 39 held in pressure contact with the peripheral surface of the ceramic heater 20 to position the ceramic heater 20 in place along with the contact springs 36. The contact plate 38 is connected through a lead wire 43 to a control circuit (not shown). The lead wire 43 is bound along with the lead wires 41 and 42 to form a harness 40.

The numeral 44 designates seal members provided in the respective through-holes 29.

Figure 2:
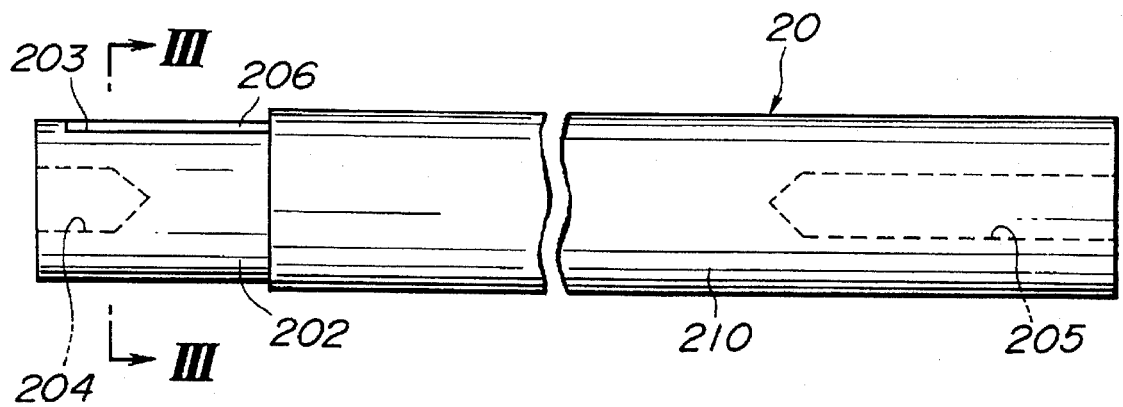
FIG. 2 is an enlarged side view of the ceramic heater.
Figure 3:
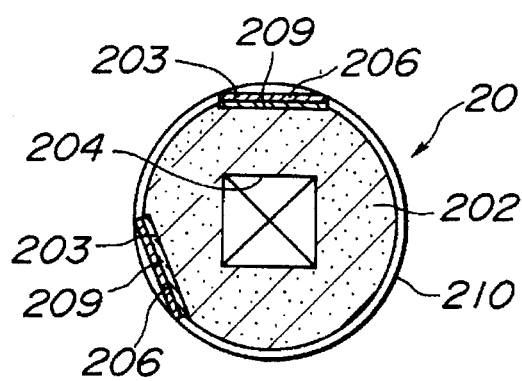
FIG. 3 is an enlarged transverse sectional view taken along the lines III—III of FIG. 1.
Figure 4:
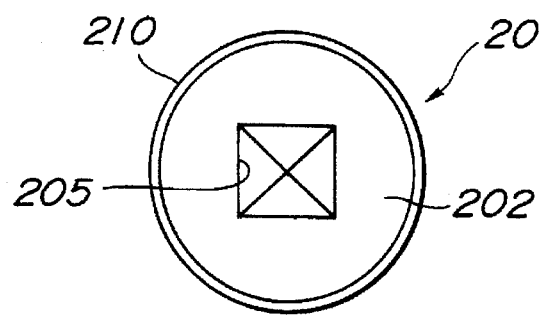
FIG. 4 is an enlarged front end view of the ceramic heater of FIG. 2.
Figure 5A:
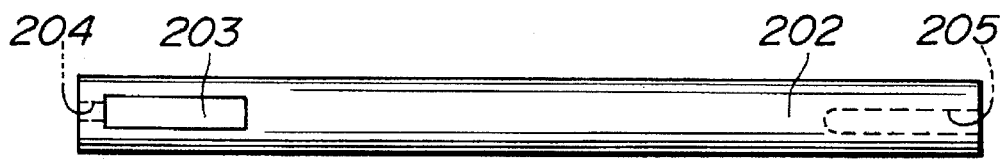
FIG. 5A shows a heater core made of a ceramic material and used in a process to produce the ceramic heater.
Figure 5B:
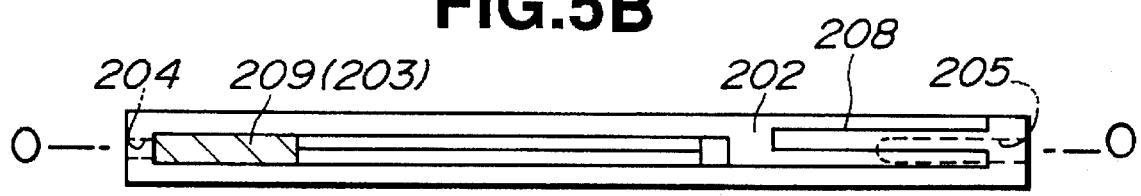
FIG. 5B shows a pattern printing process where a conductive material is printed to form a heater pattern in the production sequence of the ceramic heater.
Figure 6:
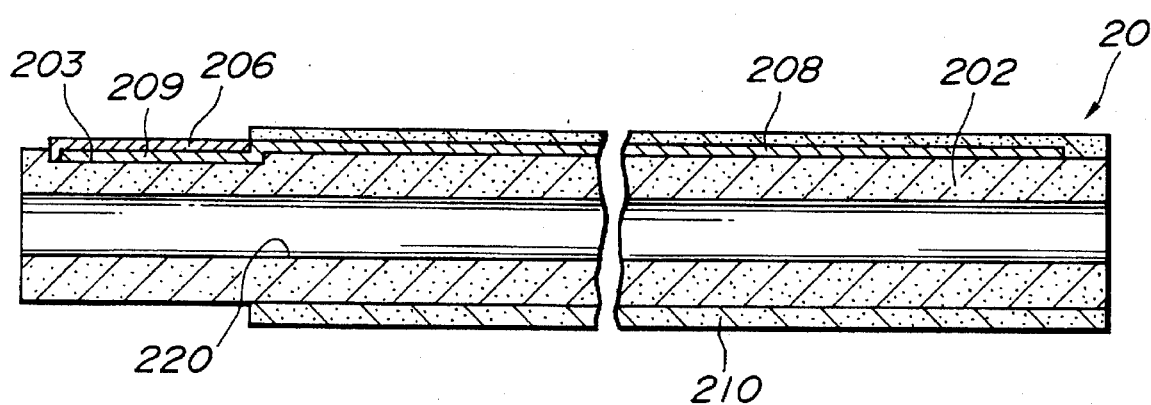
FIG. 6 is a longitudinal sectional view showing a modified form of the ceramic heater.

Referring to FIGS. 2, 3 and 4, the ceramic heater 20 includes a heater core 202 made of a ceramic material such as alumina or the like in a rod shape, terminals 206 formed on respective portions 203 flattened near the rear end of the heater core 202, a heater pattern 208 (as shown in FIGS. 5B and 6) printed on the outer peripheral surface of the heater core 202 over the area expanding from the terminals 206 to the front end of the heater core 202, and a protection layer 210 printed on the outer peripheral surface of the heater core 202 to cover the heater pattern 208. The heater core 202 is made of a ceramic material such as alumina or the like through an injection molding process. For example, the heater core 202 may be made in a cylindrical rod shape having a diameter of about 3.8 mm and a length of about 57 mm. The heater core 202 is formed near its rear end with two flattened portions 203 spaced at 120 degrees. For example, the flattened portions 203 has a width of about 1.5 mm and a length of about 6 mm. The heater core 202 is formed with a first elongated axial cavity 204 extending axially of the heater core 202 and opening at the rear end of the heater core 202 and a second elongated axial cavity 205 extending axially of the heater core 202 and opening at the front end of the heater core 202. The first axial cavity 204 may have a length of about 3 mm and the second axial cavity 205 may have a length of about 15 mm. The first and second axial cavities 204 and 205 serve to reduce the thermal capacity of the heater core 202. The terminals 206 are made of a conductive material such as gold, silver, copper, nickel or the like through a metal plating process on the respective end portions 209 of the printed heater pattern 208. The terminals 206 are connected to a power source so that the heater pattern 208 can be heated to a temperature ranging from about 500° C. to about 700° C. along with the heater core 202. Since the ceramic heater 20 extends into the sensor probe 14, the sensor probe 14 is heated to a temperature, for example, about 350° C., at which the sensor probe 14 is activated.

Figure 5C:
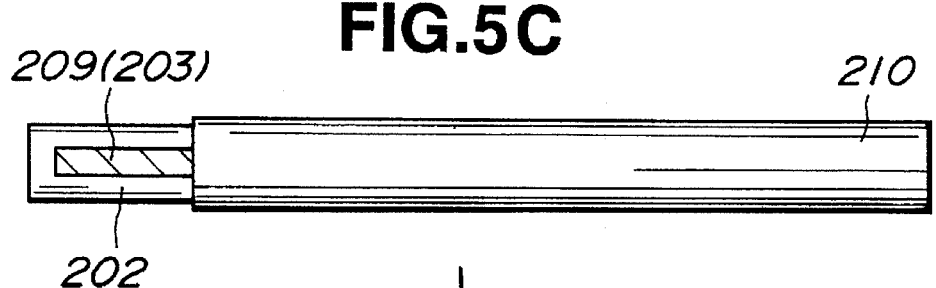
FIG. 5C shows a protection layer printing process in the production sequence of the ceramic heater.
Figure 5D:
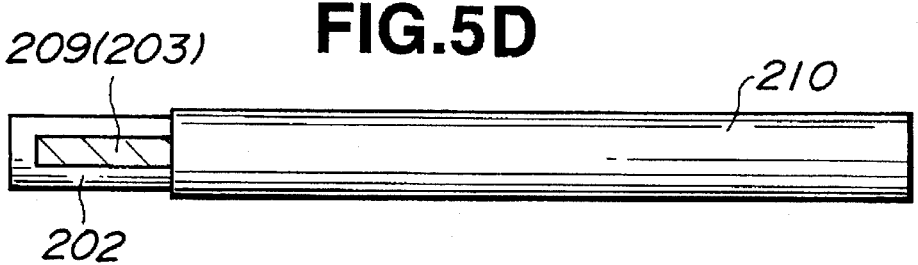
FIG. 5D shows a burning process in the production sequence of the ceramic heater.
Figure 5E:
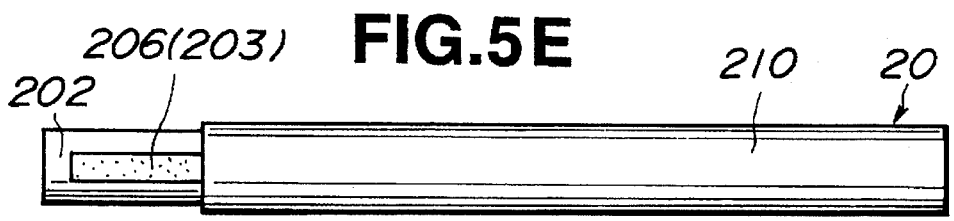
FIG. 5E shows a metal plating process in the production sequence of the ceramic heater.

Referring to FIGS. 5A to 5E, there is shown the sequence in which the ceramic heater 20 is produced. First of all, the heater core 202 is made of a ceramic material such as alumina or the like through an injection molding process, as shown in FIG. 5A. For example, the heater core 202 may be made in a cylindrical rod shape having a diameter of about 3.8 mm and a length of about 57 mm. The heater core 202 is formed near its rear end with two flattened portions 203 spaced at 120 degrees. For example, the flattened portions 203 has a width of about 1.5 mm and a length of about 6 mm. The heater core 202 is formed with a first elongated axial cavity 204 extending axially of the heater core 202 and opening at the rear end of the heater core 202 and a second elongated axial cavity 205 extending axially of the heater core 202 and opening at the front end of the heater core 202. The first axial cavity 204 may have a length of about 3 mm and the second axial cavity 205 may have a length of about 15 mm. The first and second axial cavities 204 and 205 serve to reduce the thermal capacity of the heater core 202. The flattened portions 203 and the axial cavities 204 and 205 can be integrally formed easily through such an injection molding process. FIG. 5B shows a pattern printing process where a conductive material such as tungsten or the like is printed to form a heater pattern 208 over the outer peripheral surface of the heater core 202 while rotating the heater core 202 about the axial line O—O with two support shafts (not shown) inserted in the respective cavities 204 and 205. The pattern printing process made while rotating the heater core 202 can improve the printing efficiency and the uniformity of the heater pattern 208. The printed pattern 208 includes end portions 209 formed on the respective flattened portions 203. FIG. 5C shows a protection layer printing process where a thick layer of a ceramic material such as alumina or the like is printed on the outer peripheral surface of the heater core 202 to form a protective layer 210. Preferably, the ceramic material is coated twice on the outer peripheral surface of the heater core 202 while rotating the heater core 202. The coating process made while rotating the heater core 202 can improve the uniformity of the protective layer 210. FIG. 5D shows a burning process where the protection layer 210 is burnt along with the heater core 202 in the reducing atmosphere of hydrogen containing argon gases, nitrogen gases or the like. For example the burning process may be made at a temperature of about 1600° C. to integrate the protective layer 210 on the outer peripheral surface of the heater core 202. The reducing atmosphere is effective to prevent oxidation of the rear end of the heat pattern 208 extending from the protective layer 210 during the burning process. FIG. 5E shows a metal plating process where a conductive material, such as gold, silver, copper, nickel or the like, is printed to form the terminals 206 on the respective end portions 209 of the printed heater pattern 208. Since the terminals 206 are made on the respective flattened portions 203 of the heater core 202, they can be flattened. This is effective to increase the area on which the contact springs 36 are held in contact with the respective terminals 206 so as to ensure good contact of the contact springs 36 with the respective terminals.

The operation of the oxygen sensor 10 provided with the ceramic heater 20 will be described. The oxygen sensor 10 is mounted through the externally threaded portion 13 to the engine exhaust passage with the sensor probe 14 be positioned for exposure to the exhaust gases discharged through the exhaust passage. In the presence of an oxygen concentration difference between the exhaust gases and the atmosphere, a corresponding electromotive force between its inner and outer electrodes. This electromotive force is outputted through the conductive sleeve 22, the contact plate 38 and the lead wire 43 to a control circuit (not shown) which utilizes it for air/fuel ratio feedback control. When the ceramic heater 20 is connected to a source of power through the lead wires 41 and 42 and the contact springs 36, it heats the sensor probe 14 to a temperature of about 350° C. at which the sensor probe 14 is activated. As a result, the sensor probe 14 can be activated in a short time. This is effective to ensure an accurate oxygen concentration indicative signal.

Referring to FIG. 6, there is shown a modified form of the ceramic heater 20. In this modification, the first and second axial cavities 204 and 205 are removed and replaced with an axial bore 220 extending axially through the heater core 202. This structure can further reduce the thermal capacity of the heater core 202 and thus the time required for the ceramic heater 20 to heat the sensor probe 14 to its activation temperature.

The invention has been described in detail with reference to a specific embodiment thereof, but it will be understood that variations and modifications can be effected within the scope of the invention. For example, the terminals 206 may be formed by a vacuum deposition process in place of the metal plating process. The heater pattern 208 may be made of platinum. In this case, it is not required for the protection layer to be burnt in the reducing atmosphere. Furthermore, the metal plating process required to form the terminals 206 can be eliminated when the heater pattern 208 is made of platinum.

What is claimed is:

1. A method of producing a ceramic heater, comprising the steps of:

molding a ceramic heater core in a rod shape having first and second cavities elongated axially thereof, and heater front and rear ends, wherein the first cavity opens at the rear end of the heater core, and the second cavity opens at the front end of the heater core, the heater core further having a pair of flattened portions near the rear end of the heater core;

printing a conductive heater pattern on the outer peripheral surface of the heater core while rotating the heater core about the first and second cavities, the heater pattern including end portions formed on the respective flattened portions;

printing a protective layer to cover the heater pattern except for the end portions while rotating the heater core about the first and second cavities; and burning the heater core along with the printed protective layer.

2. A method of producing a ceramic heater as claimed in claim 1, wherein the first and second cavities are connected to form a bore extending axially through the ceramic heater core.

3. A method of producing a ceramic heater as claimed in claim 1, wherein the printing of a protective layer comprises coating the ceramic heater core with a ceramic material while rotating the heater core about the first and second cavities.

4. A method of producing a ceramic heater as claimed in claim 1, wherein the printing of a protective layer comprises twice coating the ceramic heater core with a ceramic material while rotating the heater core about the first and second cavities.

5. A method of producing a ceramic heater as claimed in claim 1, wherein the heater core burning takes place in a reducing atmosphere.

6. A method of producing a ceramic heater as claimed in claim 5, wherein the reducing atmosphere comprises at least one gas selected from the group consisting of hydrogen containing argon gas or hydrogen containing nitrogen gas.

7. A method of producing a ceramic heater as claimed in claim 1, wherein the heater core burning is at a temperature of about 1600° C.

8. A method of producing a ceramic heater as claimed in claim 1, further comprising forming metal electrodes which contact at least a portion of the end portions of the heater pattern.

9. A method of producing a ceramic heater as claimed in claim 8, wherein the metal electrodes contain one or more of gold, silver, copper and nickel.

10. A method of producing a ceramic heater as claimed in claim 8, wherein the metal electrodes are formed by a plating process.

11. A method of producing a ceramic heater as claimed in claim 8, wherein the metal electrodes are formed by a vacuum deposition process.

12. A method of producing a ceramic heater as claimed in claim 1, wherein the conductive heater pattern comprises platinum.

* * * * *